(12) United States Patent
Pugia et al.

(10) Patent No.: US 7,419,665 B2
(45) Date of Patent: Sep. 2, 2008

(54) MONOCLONAL ANTIBODIES FOR DETECTION OF URINARY TRYPSIN INHIBITORS

(75) Inventors: Michael J. Pugia, Granger, IN (US); Linda Anderson-Mauser, Elkhart, IN (US); Solomon H. Murphy, Spring, TX (US); Ronald G. Sommer, Elkhart, IN (US); Shannon Gleason, Jones, MI (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 10/574,862

(22) PCT Filed: Jul. 29, 2004

(86) PCT No.: PCT/US2004/024881

§ 371 (c)(1),
(2), (4) Date: Apr. 6, 2006

(87) PCT Pub. No.: WO2005/040222

PCT Pub. Date: May 6, 2005

(65) Prior Publication Data

US 2007/0020683 A1    Jan. 25, 2007

Related U.S. Application Data

(60) Provisional application No. 60/511,835, filed on Oct. 16, 2003.

(51) Int. Cl.
*A61K 39/395* (2006.01)
(52) U.S. Cl. ............... 424/141.1; 424/130.1; 424/146.1
(58) Field of Classification Search ....................... None
See application file for complete search history.

(56) References Cited

U.S. PATENT DOCUMENTS

| | | | | |
|---|---|---|---|---|
| 6,242,197 | B1 * | 6/2001 | Papuashvili | .................. 435/7.1 |
| 6,583,108 | B1 | 6/2003 | Tamburini et al. | |
| 6,673,632 | B1 | 1/2004 | Ohshiro | |
| 2001/0055816 | A1 | 12/2001 | Rehm et al. | |
| 2002/0004219 | A1 | 1/2002 | Corey et al. | |
| 2003/0125577 | A1 | 7/2003 | Corey et al. | |
| 2003/0190732 | A1 | 10/2003 | Josic | |

FOREIGN PATENT DOCUMENTS

JP         10-70997        3/1998

OTHER PUBLICATIONS

Trefz et al.; "Establishment of an enzyme-linked immuno-sorbent assay for urinary trypsin inhibitor by using a monoclonal antibody" Journal of Immunoassay, 12(3), 347-369 (1991).*
Li et al. PNAS 77:3211-3214, 1980.*
Lederman et al. 1991, Molecular Immunology 28:1171-1181.*
Merck Manual [online]. Copyright © 1995-2007 Merck & Co., Inc., Whitehouse Station, NJ, USA. [retrieved on Apr. 18, 2007]. Retrieved from the Internet:<http://www.merck.com/mmpe/sec07/ch073/ch073c.html#sec07-ch073-ch073c-664>. Acute Coronary Syndromes (ACS); Diagnosis].*
Bast, Jr. et al. Clinical Cancer Research, 2005, 11:6103-6108.*
LaBaer et al. Journal of Proteome Research, 2005, 4:1053-1059.*
Baker Nature Biotechnology, 2005, 23:297-304.*
Pugia et al.; "Pathophysiology and diagnostic value of urinary trypsin inhibitors," *Clin Chem Lab Med*, vol. 43 (1), 2005, pp. 1-16.
Zhu et al.; "Analysis of ligand binding by bioaffinity mass spectrometry," *Clinica Chimica Acta xx*, (2006), xxx-xxx, CCA-10235; 8 pages.
Jortani et al.; "Sensitive Noninvasive Marker for the Diagnosis of Probable Bacterial or Viral Infection," *Journal of Clinical Laboratory Analysis*, vol. 18 (2004) pp. 289-295.
Pugia et al.; "The uristatin dipstick is useful in distinguishing upper respiratory from urinary tract infections," *Clinica Chimica Acta*, vol. 341 (2004) pp. 73-81.
Suzuki et al.; "Suppression of Invasion and Peritoneal Carcinomatosis of Ovarian Cancer Cell Line by Overexpression of Bikunin," *Int. J. Cancer*, vol. 104, pp. 289-302, (2003).
Capon et al.; "In acute inflammation, the chondroitin-4 sulphate carried by bikunin is not only longer; it is also undersulphated," *Biochimie*, vol. 85 (2003) pp. 101-107.
Kobayashi et al.; "Suppression of urokinase receptor expression by bikunin is associated with inhibition of upstream targets of extracellular signal-regulated kinase-dependent cascade," *Eur. J. Biochem.*, vol. 269, pp. 3945-3957 (2002).
Mizon et al.; "Urinary Bikunin Determination Provides Insight into Proteinase/Proteinase Inhibitor Imbalance in Patients with Inflammatory Diseases," *Clin Chem Lab Med 2002*, vol. 40(6), pp. 579-586, 2002.
Kreft et al.; "Polarized Expression of Tamm-Horsfall Protein by Renal Tubular Epithelial Cells Activates Human Granulocytes," *Injection and Immunity*, May 2002, pp. 2650-2656.
Suzuki et al.; "Kunitz-type Protease Inhibitor Bikunin Disrupts Phorbol Ester-induced Oligomerization of CD44 Variant Isoforms Containing Epitope v9 and Subsequently Suppresses Expression of Urokinase-type Plasminogen Activator in Human Chondrosarcoma Cells," *The Journal of Biological Chemistry*, vol. 277 (10), Mar. 8, 2002, pp. 8022-8032.
Matsumi et al.; "Changes in Urinary Trypsin Inhibitor in Blood and Urine, as Well as Serum Cytokines in Living Related Liver Transplantation," *Department of Anesthesiology and Resuscitology, Ikayama University Graduate School of Medicine and Dentistry*, Okayama 700-8558, Sep. 12, 2002, 12 pages.
Isogai et al.; "Quantitative analysis of bikunin-laden mast cells in follicular eruptions and chronic skin lesions of atopic dermatitis," *Arch Dermatol Res*, (2002) vol. 294, pp. 387-392.
Tyagi et al.; "The Liver-Specific Human $\alpha_1$-Microglobulin/Bikunin Precursor (AMBP) is Capable of Self-Association," *Archives of Biochemistry and Biophysics*, vol. 399 (1), Mar. 1, 2002, pp. 66-72.

(Continued)

*Primary Examiner*—Phillip Gambel
*Assistant Examiner*—Sharon Wen
(74) *Attorney, Agent, or Firm*—Noam R. Pollack, Esq.; Harold Wells, Esq.

(57) ABSTRACT

Certain monoclonal antibodies are able to detect urinary trypsin inhibitors (UTIs) that are characteristic of disease in humans. In particular, the UTIs include AMBK, Bikunin, Uristatin, Uristatin-1, Uristatin-2, as defined herein, also including the fragments and aggregates thereof.

9 Claims, 3 Drawing Sheets

OTHER PUBLICATIONS

Sugita et al.; "Effect of a human urinary protease inhibitor (Ulinastatin) on respiratory function in pediatric patients undergoing cardiopulmonary bypass," *J. Cardiovasic Surg.*, vol. 43(4), pp. 437-444.

Lin et al.; "Plasma and urine levels of urinary trypsin inhibitor in patients with acute and fulminant hepatitis," *Journal of Gastroenterology and Hepatology*, vol. 17, pp. 140-147; 2002.

Pugia et al.; "Clinical utility of a rapid test for uristatin," *Clinical Biochemistry*, vol. 32, pp. 105-110, 2002.

Moriyama et al.; "Expression of Inter-α Inhibitor Related Proteins in Kidneys and Urine of Hyperoxaluric Rats," *The Journal of Urology*, vol. 165, pp. 1687-1692, May 2001.

Takubo et al.; "Urinary trypsin inhibitor levels in the urine of patients with haematological malignancies," *Haematologia*, vol. 31 (3), pp. 267-272 (2001).

Suzuki et al.; "Excretion of Bikunin and Its Fragments in the Urine of Patients with Renal Stones," *The Journal of Urology*, vol. 166, pp. 268-274, Jul. 2001.

Janssen et al.; "Expression of inter-α-trypsin inhibitor and tumor necrosis factor-stimulated gene 6 in renal proximal tubular epithelial cells," *Kidney International*, vol. 60, pp. 126-136, 2001.

Mizon et al.; "The chondroitin sulfate chain of bikunin-containing proteins in the inter-α-inhibitor family increases in size in inflammatory diseases," *Eur. J. Biochem*, vol. 268, pp. 2217-2724, 2001.

Suzuki et al.; "Structure and function analysis of urinary trypsin inhibitor (UTI): identification of binding domains and signaling property of UTI by analysis of truncated proteins," *Biochimica et Biophysica Acta*, pp. 26-36, 2001.

Kobayashi et al.; "Identity of Urinary Trypsin Inhibitor-binding Protein to Link Protein," *The Journal of Biological Chemistry*, vol. 275 (28), pp. 21185-21191, Jul. 14, 2000.

Thuveson et al.; "The Low pH in Trans-Golgi Triggers Autocatalytic Cleavage of Pre-α-inhibitor Heavy Chain Precursor," *The Journal of Biological Chemistry*, vol. 275 (40), pp. 30996-31000, Oct. 6, 2000.

Mizon et al.; "Human pre-α-inhibitor is a positive acute-phase protein that is more susceptible than inter-α-inhibitor to proteolysis by stimulated neutrophils," *European Journal of Clinical Investigation*, vol. 30, pp. 79-86, 2000.

Dean et al.; "Effects of inter-α-inhibitor and several of its derivatives on calcium oxalate crystallization in vitro," *Clinical Science*, vol. 98, pp. 471-480, 2000.

Balduyck et al.; "Inflammation-induced systemic proteolysis of inter-α-inhibitor in plasma from patients with sepsis," *J. Lab Clin Med*, vol. 135 (2), pp. 188-198, Feb. 2000.

Fries et al.; "Bikunin—not just a plasma proteinase inhibitor," *The International Journal of Biochemistry & Cell Biology*, vol. 32, pp. 125-137, 2000.

Iida et al.; "Expression of Bikunin mRNA in Renal Epithelial Cells After Oxalate Exposure," *The Journal of Urology*, vol. 162, pp. 1480-1486, Oct. 1999.

Marengo et al.; "Differential Expression of Urinary Inter-α-Trypsin Inhibitor Trimers and Dimers in Normal Compared to Active Calcium Oxalate Stone Forming Men," *The Journal of Urology*, vol. 159, pp. 1444-1450, May 1998.

Bost et al.; "Intera-α-trypsin inhibitor proteoglycan family, A group of proteins binding and stabilizing the extracellular matrix," *Eur. J. Biochem*, vol. 252, pp. 339-346, 1998.

Dawson et al.; "Inter-α-inhibitor in calcium stones," *Clinical Science*, vol. 95, pp. 187-193, 1998.

Mizon et al.; "Human pre-a-inhibitor: isolation from a by-product of industrial scale plasma fractionation and structural analysis of its H3 heavy chain," *Journal of Chromatography B*, vol. 692, pp. 281-291, 1997.

Marlor et al.; "Identification and Cloning of Human Placental Bikunin, a Novel Serine Protease Inhibitor Containing Two Kunitz Domains," *The Journal of Biological Chemistry*, vol. 272 (18), pp. 122202-122208, May 2, 1997.

Delaria et al.; "Characterization of Placental Bikunin, a Novel Human Serine Protease Inhibitor," *The Journal of Biological Chemistry*, vol. 272 (18), pp. 12209-12214, May 2, 1997.

Kyoto Daiichi Kagaku Co., Ltd. Development and Production Division; "Technical Data On Methods of Measuring Urinary Trypsin Inhibitor (UTI) (Enzyme Inhibition Method)," Feb. 25, 1997, 28 pages.

Yamasaki et al.; "Uptake of human urinary trypsin inhibitor by the kidney epithelial cell line, LLC-$PK_1$," *Eur J Physiol*, vol. 433, pp. 9-15, 1996.

Salier et al.; "The inter-α-inhibitor family: from structure to regulation," *Biochem J.*, vol. 315, pp. 1-9, 1996.

Heron et al.; "Involvement of the three inter-α-trypsin inhibitor (ITI) heavy chains in each member of the serum ITI family," *FEBS Letters*, vol. 374, pp. 195-198, 1995.

Maradny et al.; "Urinary trypsin inhibitor may have a protective effect on endothelial cells in preeclampsia," *Acta Obstet Gynecol Scand*, vol. 73, pp. 755-757, 1994.

Takemura et al.; "A Clinical Study of Urinary Trypsin Inhibitor, an Acute Phase Reactant in Urine, In Acure Pediatric Infectious Diseases," *Japanese Journal of Inflammation*, vol. 14 (1), pp. 53-57, Jan. 1994.

Takemura et al.; "Acute-Phase Reactants in Urine: A Clinical Investigation of Urinary Trypsin Inhibitor in Pediatric Infectious Diseases," 108-494.

Article: Belova et al.; *Biokhimiia*, vol. 58(8), pp. 1199-11205, Aug. 1993.

Daveau et al.; "Human inter-α-inhibitor family in inflammation: simultaneous synthesis of positive and negative acute-phase proteins," *Biochem J.*, vol. 292, pp. 485-492, 1993.

Noda, Tadafumi; "The Immunochemical Assay of Human Urinary Trypsin Indicator and Its Clinical Significance As an Acute-Phase Reactant," *Journal of the Osaka City Medical Center*, vol. 41(2), pp. 489-500, Jun. 1992.

Rourt et al.; "Electrophoretic Pattern of the Inter-α-Inhibitor Family Proteins in Human Serum, Characterized by Chain-Specific Antibodies," *Biol. Chem. Hoppe-Seyler*, vol. 373, pp. 1019-1024, Oct. 1992.

Piette et al.; "Urinary Trypsin Inhibitory Activity for the Diagnosis of Bacterial Infection: A Prospective Study in 690 Patients," *EJM*, vol. 1 (5), pp. 273-276, Sep. 1992.

Trefz et al.; "Establishment of an Enzyme-Linked Immuno-Sorbent Assay for Urinary Trypsin Inhibitor by Using a Monoclonal Antibody," *Journal of Immunoassay*, vol. 12(3), pp. 347-369, 1991.

Kuwajima et al.; "Automated Measurement of Trypsin Inhibitor in Urine with a Centrifugal Analyzer: Comparison with Other Acute Phase Reactants," *Clin Biochem*, vol. 23, pp. 167-171, 1990.

Article: Nishino et al.; "Measurement of urinary trypsin inhibitor in urine, plasma and cancer tissues of patients with stomach cancer," *Haemostasis*, vol. 19(2), pp. 112-119, 1989.

Pratt et al.; "Inflammatory Cells Degrade Inter-α Inhibitor to Liberate Urinary Proteinase Inhibitors," *Journal of Leukocyte Biology*, vol. 45, pp. 1-9, 1989.

Loutfti et al.; "Urinary Trypsin Inhibitory Capacity and $\alpha_1$ Protease Inhibitor," *Ann. Biol. Clin.*, vol. 47, pp. 261-267, 1989.

Kaumeyer et al.; "The mRNA for a proteinase inhibitor related to the HI-30 domain of inter-α-trypsin inhibitor also encodes α-1-microglobulin (protein HC)," *Nucleic Acids Research*, vol. 14 (20), pp. 7839-7850, 1986.

Hochstrasser et al.; "Kunitz-Type Proteinase Inhibitors Derived by Limited Proteolysis of the Inter-α-Trypsin Inhibitor, $V^{[1-4]}$," *Hoppe-Seyler's Z. Physiol. Chem.*, vol. 362, pp. 1357-1362, Oct. 1981.

Friedman, Theodore; "Further Characterization of the Subunit of Tamm-Horsfall Mucoprotein," *Biochimica et Biophysica Acta*, vol. 130, pp. 355-360, 1966.

Dehne et al.; "Tamm-Horsfall Protein, $\alpha_1$- and $\beta_2$-Microglobulins as Micromolecular Markers of Renal Function in Cardiac Surgery," *Anaesthesist*, vol. 44, pp. 545-551, 1995.

Pfleiderer et al.; "Renal proximal and distal tubular function is attenuated in diabetes mellitus type 1 as determined by the renal excretion of $\alpha_1$-microblogulin and Tamm-Horsfall protein," *Clin Investig*, vol. 71, pp. 972-977, 1993.

Rosenmann et al.; "Tissue antigens in normal and pathologic urine samples: A review," *Kidney International*, vol. 16, pp. 337-344, 1979.

Article: Faarvang, Hans Jorgen; "Urinary Trypsin Inhibitor in Man ("Mingin")," Munksgaard, Copenhagen, 1965, 37 pages.

Dillard et al.; "The Trypsin Inhibitor of the Urine in Health and Disease," *Biochemical Laboratory, Medical School, University of Virginia*, pp. 266-271, Apr. 24, 1950.

Pugia et al.; "Analysis of ligand binding by bioaffinity mass spectrometry," Science Direct (2006) 71-78.

Pugia et al.; "Immunological evaluation of urinary trypsin inhibitors in blood and urine: Role or N-&O-linked glycoprotiens," Springer Science & Media, LLC (2006) 24:5-15.

Pugia et al.; "Bikunin (Urinary Trypsin Inhibitor): Structure, Biological Relevance, and Measurement," Advances in Clinical Chemistry vol. 44 (2007) pp. 223-245.

* cited by examiner

MONOCLONAL ANTIBODIES FOR DETECTION OF URINARY TRYPSIN INHIBITORS

Priority is claimed from PCT/US2004/024881 filed Jul. 29, 2004 which claims priority of U.S. provisional application No. 60/511,835 filed Oct. 16, 2003.

BACKGROUND OF THE INVENTION

This invention relates generally to the detection of urinary trypsin inhibitors (UTIs) in human urine. UTIs inhibit one or more of the Serine proteases. Trypsin is a member of the family of Serine proteases, i.e. enzymes, that includes trypsin, elastase, kallikrein, plasmin, thrombin, chymotrypsin, and cathepsin, among others. This group of inhibitors primarily forms after an increase in the number of white blood cells in the body due to the release of elastase during infection or inflammation. UTIs are not normally found in the urine produced by healthy individuals. The amount is elevated in those whose bodies have bacterial infections and inflammatory disorders or other maladies such as malignant tumors, kidney disease, myocardial infarction, lung emphysema, surgical trauma, and kidney stones among others.

When infections and/or inflammation occur, the bodies' response involves the production of serine proteases such as elastase released by neutrophils. Non-inhibitor forms of UTI, called pro-inhibitors, such as interleukin-$\alpha$-inhibitor (I-$\alpha$-I) and the pre-interleukin-$\alpha$-inhibitor (P-$\alpha$-I), circulate freely in plasma of healthy and diseased individuals. Serine proteases cause proteolysis of the pro-inhibitors and release the lower molecular weight UTIs into active function. The released urinary trypsin inhibitors act on serine proteases and are later excreted in the urine. Discovered in 1909, urine trypsin inhibitors are Kunitz-type protease inhibitors and have been named HI-30, Mingin, Urinastatin, Serpin, and Ulinastatin over the years with the scientific community settling on the name Bikunin for a prevalent fragment of ~30 Kda molecular weight. The amino acid sequence of the Bikunin inhibitor fragment is known. It contains two Kunitz inhibitory binding domains and a large and variable chondroitin sulfate chain. See the International Journal of Biochemistry and Cell Biology 32 (2000) 125-137.

Although the amount of urinary trypsin inhibitors has been measured by several methods, e.g. enzyme inhibition, antibody stains, latex agglutination, and radioimmunoassays, all of the UTIs in the sample are measured. It has not been shown that certain forms of the inhibitor can result from chronic disease and are more easily distinguished from the inhibitors which were present in individuals with lesser degrees of inflammation. As a result, the diagnostic use of UTIs has to date only been as a non-specific marker of infection and/or inflammation. The non-specific nature lessens the clinical utility as determination of UTIs does not help the care giver to know the type or site of infection and makes it difficult to separate conditions for which the patient would need therapy from general ailments. The present invention is directed toward making such distinctions.

One method of measuring the UTI content of a urine sample involves the addition to the sample of known amounts of trypsin and then measuring the degree to which the trypsin has been inhibited. Examples of this technique can be found in three published U.S. Patent Applications 2001/0055816 A1, 2002/0004219 A1, and 2003/0125577 A1. In these published applications, a known amount of trypsin on a substrate capable of producing a detectable response is added to a sample of urine. The substrate is cleaved by trypsin to yield detectable byproducts. If trypsin inhibitors are present, the response is diminished since some of the available substrate is not cleaved. Thus, by measuring the amount of the trypsin present and functioning relative to the amount added, the UTI content can be determined. This method detects any inhibitor of trypsin activity and is non-specific for any given trypsin inhibitor excreted into urine. The patent application published in 2001 discloses the use of a polycarboxylic chelating agent to inhibit the interference of calcium in the sample. The patent applications published in 2002 and 2003 concern certain aromatic esters of arginine shown to be useful as substrates for trypsin in the method just described.

Another method which determines directly the amount of UTIs in a urine sample involves the development of antibodies which attach themselves to the urinary trypsin inhibitors and which, by the addition of immunoassay reagents containing the antibody to a sample, produce a response signal. There are various immunoassay methods which could be used to apply antibodies of the invention such as microparticle capture immunoassays (MIC), latex agglutination inhibition (LAI), solid phase chromatographic (IC), radioimmunoassays (RIA), enzyme linked immunosorbent assays (ELISA), enzyme linked assays (EIA), fluorescence linked assays (FIA), luminescence linked assays (LIA), rare earth metals label assays, chemiluminescence assays (CLA) and optical color label assays (OA) such as colored latex particle and colloidal gold. It is also feasible to use electrochemical signal transducers (EST) based on amperometric, impedimetric, and potentimetric detection methods.

In principle, immunoassays can be of either a heterogeneous format requiring a separation step or a homogeneous format without separation and either of a competitive or a non-competitive nature. For heterogeneous assays, solid phases can be used to separate bound antigen from free antigen and can include plastic wells, tubes, capillaries, membranes, latex particles, and magnetic particles. Antibodies are attached to the solid phases. Antibodies can also be attached or conjugated (labeled) with reagents that directly or indirectly produce detectable responses, other antibodies or other reagents in a variety of fashions. An immunoassay can also employ multiple and different antibodies in a variety of manners such sandwich assays, double label assays, and multiple sandwich assays depending on the detection needs for the material being detected.

In general, the immunoassay reagents undergo changes whereby a signal is generated and the intensity of the signal generated is proportional to the concentration of the analyte measured in the specimen or sample. Immunoassay reagents contain indicator dyes, metals, enzymes, polymers, antibodies, surface active agents, particles, electrochemically reactive ingredients and various other chemicals dried or filled onto carriers. Carriers often used are tubes, cups, capillaries, strips, vials, papers, microfluidic devices, cassettes, membranes or polymers with various sample volume, uptake and transport properties.

It has been found that polyclonal antibodies produced from rabbits inoculated with urinary trypsin inhibitors purified from the urine of patients with kidney disease are useful in measuring the amount of total UTIs in urine samples from both healthy individuals and those with disease. However, the polyclonal antibodies are not able to distinguish the various forms of UTI from each other, in particular from the pro-inhibitors interleukin-$\alpha$-inhibitor (I-$\alpha$-I) and pre-interleukin-$\alpha$-inhibitor (P-$\alpha$-I). Since all these proteins are readily present in the healthy patients, the cross reactivity of the polyclonal antibody makes it useless for distinguishing diseased patients from healthy patients by using blood specimens. In the case of urine specimens, the high molecular weights of P-α-I and I-α-I make it less likely that they will pass through the kidney, thus the polyclonal antibodies were more effective in spite of their reduced specificity. However due to the non-specific nature of the polyclonal antibodies they have not been found to be more effective than the general enzyme inhibition method previously discussed. The polyclonal antibodies were cross-reactive to all forms of UTI in urine and not specific to any one form and would measure both inhibitory and non-inhibitory UTI.

In Journal of Immunoassay 1991; 12:347-69, Trefz et al disclose the use of a monoclonal antibody produced from mice immunized with high molecular weight (240 kDa). Inter-α-trypsin inhibitor (an inactive pro-inhibitor) in an enzyme-linked immunoassay (ELISA). The results showed that the method was effective to distinguish between healthy individuals and those with disease, since the level of UTIs in the urine of those individuals with disease was higher than those without disease. The authors noted that Inter-α-trypsin inhibitor (ITI) having a molecular weight of about 240 kDa, contained several lower molecular weight peptides, understood to result from disintegration of the ITI. Their monoclonal antibody, IATI5, was found to recognize three major bands, a 240 kDa, a 120 kDa, and a 50 kDa band. In a purified HI-30 preparation their monoclonal antibody detected a protein of about 33 kDa.

In their work reported in the Journal of Biological Chemistry, Vol. 275, No. 28, issue of July 14, pp. 21185-21191, 2000, Hirashi Kobayashi et al. compared polyclonal and monoclonal antibodies raised against a purified preparation of UTI that was shown to have molecular weight in the range of about 40-80 kDa in SDS-PAGE and Western blotting. Derivatives were found to have molecular weights of about of 7 kDa, 30 kDa, and 60 kDa.

During the cross-reactivity studies of a polyclonal antibody for UTI prepared by Bayer, we were surprised to discover that further breakdown of the inhibitory Bikunin occurs during the acute phase infections in patients leading to the formation of other inhibitory UTIs containing both Kunitz inhibitor domains, but lacking the chondroitin sulfate chain. This UTI, termed Uristatin, has a molecular weight of ~17 kDa. In a paper (Clinical Chemistry Acta (2004) 341, 73-81) reporting tests with a dipstick for detecting urinary trypsin inhibitors, Pugia et al showed that the dipstick reported the presence of two forms for UTIs; Bikunins and Uristatins. They identified the typical molecular weight of Bikunin (30.9 kDa) and three key forms of the Uristatin, designated Uristatin-1 (5.9 kDa), Uristatin-2 (8.5 kDa) and the combination of Uristatin-1 and Uristatin-2 which was termed Uristatin (17.4 kDa). All forms of Uristatin lack the chondroitin sulfate chain, and are very prevalent in patient specimens when analyzed by electrophoresis. All Uristatin forms are inhibitory to the trypsin family of proteases; therefore they contain at one of the two Kunitz inhibitory domains that inhibit the protease active site upon binding. Uristatin-1 contains binding domain 2 and Uristatin-2 contains binding domain 1.

It was further noted that, given the conditions of the patient used for collection, the typical molecular weights of IUTIs could vary considerably. Additional variations of Bikunin and Uristatin are due to fragmentation of peptide structure, variations in the peptide sequence and variations in carbohydrate sequences attached to the Bikunin and Uristatin. Variations in molecular weight resulting from fragments occur by cleavage of the peptide sequence. A high degree of fragmentation is expected during inflammation as the inhibitors are exposed to the proteases that can cause cleavage. Elongation and fragmentation of the carbohydrate portions was also expected during inflammation as the glycoprotein are metabolized by a number of glycosyl transferases and glycosidases causing a great number of possible variants to the chondroitin sulfate chain attached to Bikunin and to the sugar side chains attached to Uristatin. Additional variations also occur by aggregation of the fragments into diners or higher oligomers, especially through association and metabolism of the carbohydrate portions. Therefore the functional UTI proteins represent a range of possible proteins around a typical molecular weight.

An additional protein in this suprafamily is the precursor protein (AMBK) that initiates the biosynthesis of the inhibitory and pro-inhibitor forms. This protein is present in the plasma of patients when the genes signal up-regulation to initiate the biosynthesis. The AMBK contains the Bikunin but lacks the heavy chains that inactivate the inhibitory domains and is attached to alpha-1-microglobulin. The detection of this form of the inhibitor is also important in determining the body's response to inflammation and infection.

There remains a need for a method of measuring specific urinary trypsin inhibitors that is able to detect the presence of disease by determining certain characteristic UTIs not found in healthy individuals. The present inventors have developed a method for making such determinations by using certain monoclonal antibodies, as will be described in detail below.

SUMMARY OF THE INVENTION

The invention includes certain monoclonal antibodies that are able to attach themselves to inhibitory urinary trypsin inhibitors (UTI) characteristic of disease in humans and that can be detected by standard analytical techniques, including MIC, LAI, IC, ELISA, EIA, RIA, LIA CLA, OA and EST (acronyms defined above) in both heterogeneous and homogeneous assays. These monoclonal antibodies are characterized by their ability to allow direct or indirect measurement of urinary trypsin inhibitors such as Bikunin, Uristatin, Uristatin-1 Uristatin-2 and AMBK in the presence of other common proteins in urine and serum such as Human Serum Albumin (HSA), Tamm-Horsfall protein (THP), α-1-microglobulin (α-1M), α-1-antichymotrypsin (α-1ACT) and non-inhibitory urinary trypsin inhibitors (pro-inhibitor forms) such as I-α-I and P-α-I.

Direct measurement of a UTI may be obtained by either using antibodies that recognize only that particular UTI. Indirect measurement of a UTI may be made by subtraction using antibodies that recognize UTIs other than the one of interest and antibodies that recognize all or most of the prevalent UTIs. In the examples below, antibodies secreted by hybridoma ATCC 421-3G5.4C5.3B6 and hybridoma ATCC 421-5G8.1A8.5C1 are shown to be suitable for determining the amount of UTIs in both urine and blood while hybridoma ATCC 420-5D11.5G8.1E4 is suitable for correction of cross reactivity and determining the amount of UTIs. Other antibodies will be shown to have similar characteristics.

Such monoclonal antibodies may be made by introducing purified UTIs into mice as an immunogen. Single hybridoma clones producing only one antibody have been created by carrying out the procedure of Kohler and Milstein. The characteristic properties of the monoclonal antibodies have been studied, using the Surface Enhanced Laser Desorption/Ionzation (SELDI) technique, ELISA, and other immunoassay methods.

In another aspect, the invention includes methods of using the novel monoclonal antibodies to detect and measure forms of urinary trypsin inhibitors of interest, that is, those characterizing persons having disease. Where a monoclonal antibody is specific to an inhibitory UTI, e.g. to Bikunin, and Uristatin, or to the precursor AMBK, they can be measured directly. When a monoclonal antibody is able to bind to more than one UTI, then by using more than one antibody, the content of a particular UTI of interest may be determined by difference. The three monoclonal antibodies referred to above have been found to bind preferentially to Uristatin and Uristatin-1 and -2 but not to the pro-inhibitors.

Analyses may be carried out on samples of many biological fluids, including but not limited to blood, urine, water, saliva, spinal fluid, intestinal fluid, food, and blood plasma. Blood and urine are of particular interest.

DESCRIPTION OF THE PREFERRED EMBODIMENTS

Definitions

Figure 1:
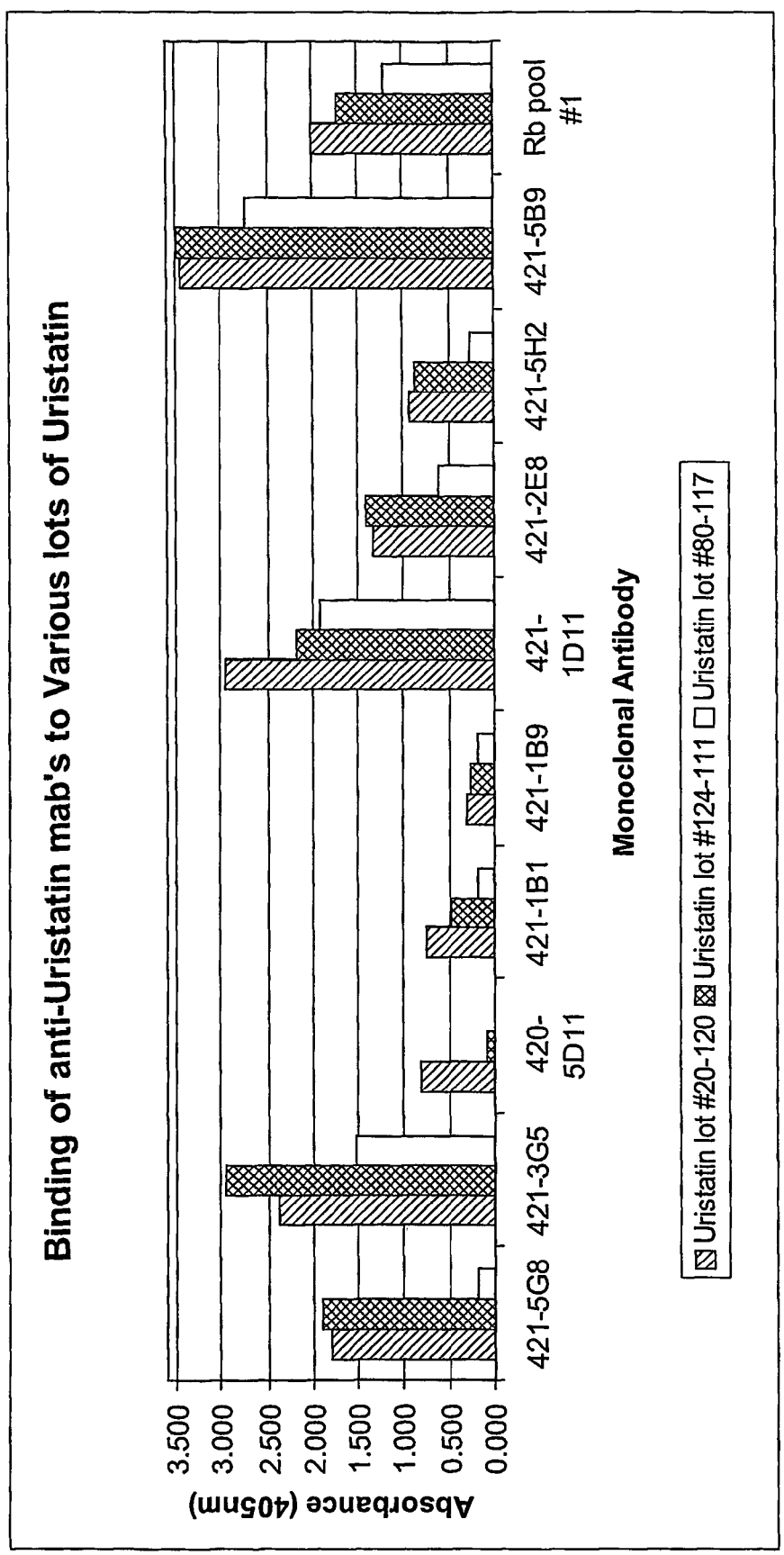
FIG. 1 is a bar chart of the results of Example 5.

Since the literature has employed various names for enzyme inhibitors, the following will provide definitions for the terms as used herein. It has been found that many variants have been detected in the SELDI® analysis discussed below. Consequently, it is believed that the definitions should encompass, not only the principal molecular weight of these inhibitors, but also a range of related molecular weight proteins.

Urinary Trypsin Inhibitors (UTIs) means all the inhibitors identified as inhibiting the serine proteases, including without limitation Bikunin, HI-30, AMBK, Uristatin, Uristatin-1, and Uristatin-2 including fragments and variants and aggregates that are capable of inhibition.

HI-30 means a fragment of higher molecular weight urinary trypsin inhibitors that may or may not be identical to bikunin and aggregates. Its monomer molecular weight is reported to be 30 kDa with a range of 21 to 46 kDa for fragments and variants.

AMBK means the protein precursor of pro-inhibitors which has three connected proteins namely the inhibitor portion (HI-30) plus alpha-1-microglobulin plus a 25 kDA unidentified protein and has a molecular weight of about 66 kDa with chondroitin sulfate and 42 kDa without chondrotin sulfate, in range of 42 to 70 kDa. It is considered to be within the definition of UTI for purposes of the invention, without regard to its function in the biosynthesis of inhibitory serine proteases.

Tamm-Horsfall glycoprotein means the glycoprotein also known as uromucoid commonly found in urine and having a typical molecular weight of about 85 kDa with a range of 80 to 91 kDa and including the various fragments and variants of.

Bikunin means a protein consisting of one or two proteinase inhibitor domains of the Kunitz type that can be connected by a short peptide chain and extended by N- and C-terminated polypeptide chains. The protein is linked to a sulphated chondroitin chain and to an oligosaccharide and has a molecular weight of about 33 kDa (range of 21-46 kDa). The structure is shown by Pugia et al in Clinical Biochemistry 32 (2002) 105-110 and the 2000 paper by Fries and Blom in the International Journal of Biochemistry & Cell Biology discussed above. The calculated molecular weight of Bikunin is 30.9 kDa in the presence of both the chondroitin sulfate chain (13.5 kDa) and the sugar side chains (1.9 kDa); these values are based on previously published sequences for HI-30.

Uristatin means a protein fragment of Bikunin resulting from cleaving the chondroitin sulfate chain from Bikunin and having a monomeric molecular weight of about 17 kDa with a range of 11 to 22 kDa for fragments and variants. The calculated molecular weight of Uristatin is 17.4 kDa lacking the chondroitin sulfate chain (13.5 kDa); these values are based on previously published sequences for HI-30.

Uristatin-1 and -2 mean protein fragments of Uristatin which contain either of the Kunitz type inhibitor domains 1 or 2 and have a monomer molecular weight of about 6 kDa with a range of 2 to 9 kDa for fragments and variants and about 8.5 kDa with a range of 2 to 12 kDa for fragments and variants respectively. The calculated molecular weight of Uristatin-1 and -2 are 5.9 kDa and 8.5 kDa respectively; the values are based on previously published sequences for HI-30.

Pro-inhibitors mean the non-inhibiting form of the protein precursor of Urinary trypsin inhibitors, including without limitation such as proteins such as I-α-I and p-α-I. These forms are considered inactive UTIs as their measured inhibitory activity is several fold less than Bikunin and Uristatin forms. They are present in healthy and infected patients.

I-α-I means Inter-α-inhibitor, understood to refer to Bikunin attached to two heavy chains, typically $H_1$ and $H_2$, by means of the chondroitin sulfate chain with a typical molecular weight of 180-240 kDa. P-α-I means Pre-α-inhibitor, understood to refer to Bikunin attached to one heavy chain, typically $H_3$ with a typical molecular weight of 125 kDa. The inter-alpha-inhibitor and pre-alpha-inhibitor group are distinct assemblies of Bikunin with heavy chains from a distinct set of four or more heavy (H) chains designated H1, H2, H3, H4, and etc. These H chains are encoded by a set of evolutionarily related H genes, and bikunin is encoded by an alpha-1-microglobulin/Bikunin precursor gene (AMBK).

Monoclonal Antibodies

Monoclonal antibodies are distinguished from polyclonal antibodies in being identical and capable of attaching themselves to a single epitope of an antigen. Polyclonal antibodies, in contrast, are not identical and therefore are not able to provide the precise analysis for which monoclonal antibodies are valuable. Monoclonal antibodies may be produced by the method of Kohler and Milstein, Nature 256:495 (1975). An immunogen (antigen) of interest is injected into mice and the B-cell lymphocytes produced in response to the immunogen are harvested after a period of time. The B-cells are combined with myeloma cells obtained from mice and introduced into a medium which permits the B-cells to fuse with the myeloma cells, producing hybridomas. These fused cells (hybridomas) are then placed in separate wells in microtiter plates and grown to produce monoclonal antibodies. The monoclonal antibodies are tested to determine which of them are suitable for detecting the antigen of interest. After being selected, the monoclonal antibodies can be grown in cell cultures or by injecting the hybridomas into mice.

Making and Separating Preferred Monoclonal Antibodies

Mice are injected with purified UTIs as the analytical target. Antibody producing cells are taken from the animals. Antibody-producing cells are fused with cells that grow continuously in culture to form hybridomas. A single hybridoma produces only one antibody. A single hybridoma divides to produce a large population of 'clones' all making the same "Monoclonal" antibody. Living hybridomas are frozen indefinitely in liquid nitrogen.

The particular procedures used by the present inventors to prepare monoclonal antibodies are described in detail in the examples. It will be understood by those skilled in the art that those procedures can be modified or augmented and that they are not to be considered to limit the scope of the invention. For example, other techniques for both immunization and fusion protocols which yield hybridomas are familiar to workers in the field of monoclonal antibodies.

The present invention involves monoclonal antibodies that were selected on the basis of their ability to bind to one or more UTIs and also preferentially to bind to certain epitopes on the intact molecule which then appear on particular fragments once the break-down of the UTIs occurs.

Detecting Trypsin Inhibitors in Biological Fluids, e.g. Urine

Once the selective monoclonal antibodies have been located, they may be grown by conventional procedures and used in ELISA testing, or any other immunoassay technique described earlier to detect the presence of UTIs that are characteristic of infection and/or inflammation.

ELISA (enzyme-linked immunosorbent assay) provides a very sensitive method for detecting antigens. In an antigen down ELISA, a microtiter plate receives a sample suspected of containing a certain antigen. After allowing for adsorption of the antigen onto the plate, and washing off all non-bound materials, the monoclonal antibody is added, incubated so that it can bind to the antigen and the excess washed off. The added monoclonal antibody may have already been labeled with a reporter molecule to permit the generation of a signal to be read by any number of techniques. Alternatively a ligand capable of attaching to the antibody (e.g. an anti-mouse antibody conjugated to a reporter molecule) is added. After excess of the enzyme-coupled ligand has been washed off, the chromogen or other substrate is added if necessary and the color developed used as an indicator of the amount of antigen present.

There are various immunoassay methods that could be used to apply antibodies of the invention such as microparticle capture immunoassays (MIC), latex agglutination inhibition (LAI), solid phase chromatographic (IC), radioimmunoassays (RIA), enzyme linked immunosorbent assays (ELISA), enzyme linked assays (EIA), fluorescence linked assays (FIA), luminescence linked assays (LIA), rare earth metals label assays, chemiluminescence assays (CLA) and optical color label assays (OA) such as colored latex particle and colloidal gold. It is also feasible to use electrochemical signal transducers (EST) based on amperometric, impedimetric, and potentimetric detection methods.

EXAMPLE 1

Preparation of Monoclonal Antibodies

BALB/c mice were immunized with 100 μg/mouse of purified UTIs obtained from renal patients by SciPac Ltd. Sittingbourne, Kent, UK, product code P250-1 to produce a response. After one month, ocular bleeds were taken from each mouse and titered by ELISA against the immunogen to assess the immune response. The mice showing the best response were boosted by injection of 100 μg/mouse with the immunogen. After four days, mice were sacrificed and their spleens used for fusion according to the method of Kohler and Milstein, Nature 256:495 (1975). The spleenocytes were fused with SP2-0 Ag14 myeloma cells using PEG (polyethylene glycol) solution with a ratio of spleenocytes to Myeloma cells of 5:1 and plated into 96 well plates using 50% PEG/HAT growth media. After 7-10 days of incubation at 37 degrees Celsius, fusion cultures were monitored for growth by feeding every 3-4 days utilizing the HAT (hypoxanthine, aminopterin, thymidine) selection method followed by subculturing with HAT growth media.

After 2-3 weeks, the wells having hybridoma colony growth were tested by ELISA to determine which growths produced an antibody immune response to the uristatin peptide. The 96 well plate cultures were tested with the uristatin peptide at 1 ug/mL coated plates. After coating plates overnight at 2-8° C., all plates were washed and blocked. Cell culture supernatants were then applied 100 μl/well for one hour at room temperature. After washing plates, Goat anti-mouse IgG Horse Radish Peroxidase at 1:2000 dilution was applied at 100 μL/well for one hour. Plates were washed once again followed by OPD (o-phenylene diamine dihydrochloride) substrate and read at 490 nm on a Spectra Max® plate reader.

The colonies giving a positive response were transferred to 24 well plates for further expansion and retesting to verify the positive results. The colonies testing positive were further expanded in six well plates in Iscove's Modified Dulbecco's Medium (IMDM) with 10% Fetal Bovine Serum (FBS). After expansion, the colonies were frozen at −70° C. and then transferred to liquid nitrogen for long-term storage.

Based on ELISA results using the purified UTIs, various clones were further expanded in IMDM, 10% FBS and frozen down.

EXAMPLE 2

Screening Procedure of Polyclonal Antibodies

Rabbit polyclonal antibodies raised against the purified UTIs were used in the screening process as this antibody was expected to be non-specific for any given form of UTIs. Serum and urine specimens from three patients with infection and two healthy controls were characterized by western blot tests using these polyclonal antibodies. The western blot tests used the commercial pre-cast gel system (Invitrogen, San Diego Calif.). Urine and plasma specimens were loaded with 1 μg and 5 μL per lane. The western blots were stained with a WesternBreeze® chromogenic immunodetection kit (from Invitrogen) following the manufacturer's instructions. Rabbit anti-UTI antiserum was used at a dilution of 1:250 000 as the primary antibody in the western blot analysis (See Table 1). These western blot results demonstrated that the rabbit polyclonal antiserum body detected Uristatin, Bikunin, AUBK, TBP, P-α-I, and I-α-I. The THP cross reactivity was unexpected and likely due to a common peptide sequence between the urinary trypsin inhibitors and THP.

TABLE 1

Results of western blot analysis using polyclonal serum as interrogating antibody of specimens

| Specimen | Major proteins observed in urine | Minor proteins observed in urine | Major proteins observed in plasma | Minor proteins observed in plasma |
|---|---|---|---|---|
| Patient 1 | Uristatin | Bikunin, AMBK, THP | P-α-I, I-α-I, | AMBK, Bikunin |

TABLE 1-continued

Results of western blot analysis using polyclonal serum as interogating antibody of specimens

| Specimen | Major proteins observed in urine | Minor proteins observed in urine | Major proteins observed in plasma | Minor proteins observed in plasma |
|---|---|---|---|---|
| Patient 2 | Bikunin | Uristatin, AMBK, THP | P-α-I, | AMBK, Bikunin |
| Patient 3 | Bikunin | Uristatin, AMBK, THP | P-α-I, | I-α-I, AMBK, Bikunin |
| Healthily control 1 | None | THP | P-α-I, | I-α-I, AMBK |
| Healthily control 2 | Bikunin | THP, P-α-I, I-α-I, AMBK and THP | P-α-I, I-α-I, | AMBK, Bikunin |

These western blot tests also demonstrated that Uristatin was better able to differentiate diseased patients from healthy controls than Bikunin, P-α-I, I-α-I, AMBK and THP. All patients and controls had THP in the urine. Similarly all had P-α-I, I-α-I, and AMBK in the plasma. The results showed that Bikunin was found in the urine of the three patients with infections but also in the urine of one control subject. We found Uristatin in all three patients but not any of the control subjects. Also we found marked increase of Uristatin in one patient. The results showed that AMBK was found in the urine of the three patients with infections but also in the urine of one control subject. This supports our belief that specific forms of UTIs can be more related to disease in certain patients than others. It should be noted here that Bikunin and especially Uristatin are in much lower concentration in blood than the pro-inhibitors I-α-I and P-α-I because they pass readily into the kidneys. The pro-inhibitors do not pass through the kidneys into urine in significant amounts, making it easier to detect Uristatin and Bikunin in urine than in blood. THP is excreted in the proximal tubules of the kidney, therefore not required to pass through the kidney, and is the most common protein in the urine as evidenced by presence in patients and controls tested. The high cross reactivity of the polyclonal method does not allow detection of the lower concentrations of Bikunin or Uristatin in blood or urine.

The presence of urinary trypsin inhibitors has been shown to be meaningful in a number of diseases. These disease include infection (pneumonia, urinary tract infection, upper respiratory tract infection, neonatal sepsis, meningitis, appendicitis, bacterial infections, bone and joint infections), acute inflammation (trauma, kidney stones, surgical truama, cardiopulmonary bypass, myocardial infarction, and burns), chronic inflammation (rheumatoid arthritis, lung emphysema, inflammatory bowel disease, pancreatitis, Crohn's disease, and as a risk factor for cardiovascular disease), neoplasia (leukemia, multiple myeloma, non-hodgkins lymphoma, ovarian cancer, breast cancer, pancreatic cancer, stomach cancer, colon cancer), and kidney disease.

Clinical value is assessed by the ability of a method to detect the urinary trypsin inhibitor forms more prevalent in disease. Also methods able to work not only in urine but also in blood would be of additional clinical value. Blood is the preferred fluid for clinical laboratory analysis allowing consistency in results, while urine is the preferred fluid for allowing non-invasive sampling at the point of care.

Therefore, an immunoassay which detects only specific forms of UTI's, such as Uristatin, Bikunin, and AMBK but not P-α-I, I-α-I or THP would have clinical utility. The results of our tests also showed that no detectable P-α-I or I-α-I was in urine but was present in all plasma specimens from controls and patients. Any immunoassay of blood for active UTIs such as Uristatin, Bikunin and AMBK should not detect P-α-I or I-α-I. The predominant bands in blood corresponded approximately to an AMBK of 63 kDa, P-α-I of 115 to 125 kDa, and I-α-I of 220 kDa in both patients and controls.

All the monoclonal antibody clones were screened based on their ability to bind UTIs in the ELISA assay using the procedure described in Example 1 and the patterns observed in western blot tests for antibodies using patient and healthy specimens as described in Table 1. The antibodies were grouped by similarity of patterns into three groups and the best representative antibodies of each group selected based on ELISA testing against the UTIs standard. The selection of clones for further study were as follows, from group A: 421-305, from group B: 421-508, and from group C: 420-5D11. For the selected mother colonies, cell culture supernatants were cloned out twice using the limiting dilution method assure that the antibodies were monoclonal. The hybridomas secreting these monoclonal antibodies in Iscove's Modified Dulbecco's Medium (IMDM) 30% Fetal Bovine Serum (FBS), and 10% Dimethyl Sulfoxide (DMSO) were deposited at the American Type Culture Collection, Mannassas, VA 20110-2209, USA on Jul. 28, 2006 and designated as ATCC 421-5D11.5G8.1E4, ATCC 421-3G5.4C5.3B6, and ATCC 421-5G8.1A8.5C1. The patent Deposit Designations are PTA-7744, PTA-7746, PTA-7745 respectively. The receipt comfirms the deposited materials will be available once a U.S. Patent has issued.

EXAMPLE 3

Characterization of Monoclonal Antibodies Against Purified Uristatin and Bikunin Standards The urinary trypsin inhibitors were produced by SciPac Ltd for our study (Sittingbourne, Kent, UK, product code P205-1); these are purified from the urine of patients with chronic renal failure. The standards were characterized by SDS-PAGE. We used a commercial pre-cast gel system (Invitrogen, San Diego Calif.) 4-12% NuPAGE® Bis-Tris with a MES (2-morpholinoethanesulfonic acid) running buffers (reducing and non-reducing), following exactly the manufacturer's procedure. Specimens were loaded at 2 μg per lane. Estimations of the proteins' molecular weights were based on a full set of standards: MagicMark12™ (Invitrogen) and SeeBlue®Plus2 (Invitrogen). Protein bands were stained with Colloidal Blue® (Invitrogen).

The results of these tests showed that UTI lot 20-120 contained 15-20% 17 kDa proteins, 50-55% 35 kDa proteins, and 25-30% 60-80 kDa proteins. UTI lot 124-111 had about 85% of the material as the 17.4 kDa band (Uristatin) but also contained amounts of Uristatin-1 (5.9 kDa) and 10-15% of Bikunin (30.9 kDa) but no AMBK was seen. UTI lot 80-117 contained substantially only 17 kDa Uristatin material.

These initial results were further refined by the SELDI® technique discussed below. It was found that UTI lot 20-120 contained 10% of 2-12 kDa proteins (Uristatin 1 & 2), 15% of 17 kDa proteins (Uristatins), 45% of 35 kDa proteins (Bikunin), and 30% of 60-80 kDa (AMBK or THP) proteins. UTI lot 124-111 had about 80% of the material as the 17.4 kDa band (Uristatin) but also contained amounts (10%) of Uristatin-1 and 2 (5.9 kDa) and 10% of Bikunin (30.9 kDa) but no AMBK was seen to be present. UTI lot 80-117 containing substantially only the 17 kDa Uristatin material and less than 2% of other molecular weight ranges.

The urine samples for the controls were assayed by the ELISA assay described in Example 1 using the three monoclonal antibodies selected in Example 2 and a Goat Anti-Mouse secondary antibody conjugate. The results for group A clone 421-3G5, group B clone 421-5G8 and group C clone 420-5D11 are shown in Table 2 and compared to the polyclonal antibody as a control.

The measurements made of color developed by the OPD substrate indicated the amount of the monoclonal antibody bound to UTIs in the standards just described, whose contents were determined by molecular weights using the western blot method and SELDI®. The values were normalized using the polyclonal antibody values and are presented in the table below as percent relative to the polyclonal antibody results.

limited to a mechanism, it is believed that binding by this monoclonal antibody does not occur through a common amino acid region between THP and Bikunin or Uristatin.

The monoclonal antibody 421-3G5 bound strongly to all UTI lots and similar to the non-specific polyclonal antibody with the notable exception of lacking reactivity to P-α-I and I-α-I. Thus 421-3G5 would be a measure of total UTI.

EXAMPLE 4

Testing of Monoclonal Antibodies with Clinical Specimens

Urine samples were obtained from patients having bacterial infections and from control patients having no such infections. The patients without infections are the "group 1" patients. To be included in the study, we only required a negative urine and blood culture ($10^5$ organisms/mL) and a normal blood white blood count (CBC). The second group of patients ("group 2") included those with infections either upper respiratory tract or urinary tract, a conclusion based on a positive complete blood count (CBC) in all. Clean-catch midstream urine collections were obtained from all patients and controls. Specimens were stored at 4° C. until tested; but if not tested within 24 hours, storage was at −70° C. until tested. For all subjects, the evaluation of urine sediment, gram stain and urine microbiological culture were always performed on the day of collection. We collected EDTA-anticoagulated blood from group 2 and performed a CBC, a high sensitivity CRP (Dade Behring, Immunoassay for C-reactive

TABLE 2

ELISA Results with Specimens from Patient and Healthy Individual and Protein Standards for UTIs.

| Specimen | 2–12/17/35/ 60–80 kDa % | ANTIBODY GROUP B CLONE 421-5G8 | ANTIBODY GROUP C CLONE 420-5D11 | ANTIBODY GROUP A CLONE 421-3G5 | POLYCLONAL ANTIBODY |
|---|---|---|---|---|---|
| UTI Standard lot 20-120 | 10/15/45/30 | 92% | 100% | 71% | 100% |
| UTI Standard lot 124-111 | 10/80/10/0 | 100% | 13% | 100% | 94% |
| UTI Standard lot 80-117 | 0/100/0/0 | 5% | 0% | 48% | 74% |

The monoclonal antibody 421-5G8 bound strongly to UTI lots #124-111 and #20-120 to a similar degree, but only bound weakly to Lot #80-117. This would be consistent with binding to the 2-12 kDa material (Uristatin 1 or 2) in both lots but not-in lot 80-117 containing only the 17 kDa material (Uristatin). Thus, this antibody appears specific for Uristatin 1 or 2 over Bikunin and Uristatin. While not wanting to be limited to a mechanism, it is believed that binding by this monoclonal antibody does not occur through the sulfated chondroitin chain. The binding is thought to be direct to an inhibitory amino acid sequence.

The monoclonal antibody 420-5D11 bound strongly to UTI lot #20-120, very weakly to lot #124-111, and did not bind to lot 80-117. This is consistent with binding to the 80 kDa material (THP) in lot #20-120, since only lot #20-120 contains a large amount of this material. If the antibody were specific for Uristatin or Bikunin also, one would expect it to have strongly responded to lot #124-111, which contained about 65% of Uristatin. This antibody appears to bind to THP but also to Bikunin and Uristatin. While not wanting to be protein) test, and a blood culture and performed all these tests on the day of blood collection.

The urine samples were also assayed by an ELISA assay using the same polyclonal antibodies as in Example 2. The antibodies were immobilized in polystyrene membrane wells of the high binding microtiter plates (PN 3690 Corning Life Sciences, Acton, Mass.), then wells were coated with Super Block® (Pierce Chem Co., Rockford Ill.) to ensure none of the following additions attach directly to the plate, then contacted with a urine sample from each patient to bind the antibodies to the UTIs in the sample. The UTI-antibody complex was reacted with a second antibody (goat anti-rabbit antibody) conjugated to alkaline phosphatase, then the unbound conjugated antibody was washed away with TBS/ 2% TWEEN-20 (ELISA Wash buffer, Upstate Cell Signaling Solutions, Lake Placid N.Y.) and the immobilized antibody assayed by determining the alkaline phosphatase on the plate by hydrolysis of PNPP (p-Nitrophenyl Phosphate, Disodium Salt) forming an absorbance at 405 nm (yellow) color upon addition of Diethanolamine Buffer (Pierce Chem Co.). The absorbance was measured a spectrophotometric micro titerplate reader (SpectroMax.® Molecular Devices Corporation, Sunnyvale, Calif.).

It was found that three control urine samples contained 51.4, 27.9 and 24.8 μg/mL of UTI proteins (Bikunin, Uristatin, and AMBK), while two samples from patients having bacterial infections contained 148 and 49.5 μg/mL. This result confirms the previous western blot test findings that polyclonal antibody gave poor separation of patients with infections from healthy controls as would be expected by the cross-reactivity between P-α-I, I-α-I and THP proteins and the desired measured proteins Bikunin, Uristatin, and AMBK.

Measurements of UTI's in the urine and plasma of patients can be made specific by the direct method and the indirect subtraction method using monoclonal antibodies, such as those shown in Table 2. As an example of direct method, Uristatin 1 or 2 in either a urine or blood specimen can be measured directly with clone 421-5G8 over the other UTI, THP and pro-inhibitors present. An additional example of direct method, all of the UTIs (IUTI) in either a urine or blood specimen can be measured directly with clone 421-3G5, but not the pro-inhibitors. An example of indirect method would be subtraction of one or more specific results from a total measurement of UTI. For example, to measure the Bikunin in patient 1's urine, Uristatin 1 or 2 would be measured directly with clone 421-5G8 and would be subtracted from a total IUTI 421-3G5 to arrive at the amount Bikunin and AMBK. Additionally any cross-reactivity to THP can measured directly with clone 420-5D11 and could be subtracted from an UTI antibody with cross reactivity to THP, such as the polyclonal antibodies, to arrive at the amount of UTI. A total measurement could be made by the polyclonal antibody as discussed above, monoclonal antibody clone 421-3G5 or the enzyme inhibition method. In the case of the polyclonal antibody, it was shown that this total was affected by the pro-inhibitor amounts, therefore the monoclonal antibody clone 421-3G5 or enzyme inhibition method would be preferred or a correction by subtraction of a pro-inhibitor result could be used.

EXAMPLE 5

Figure 2:
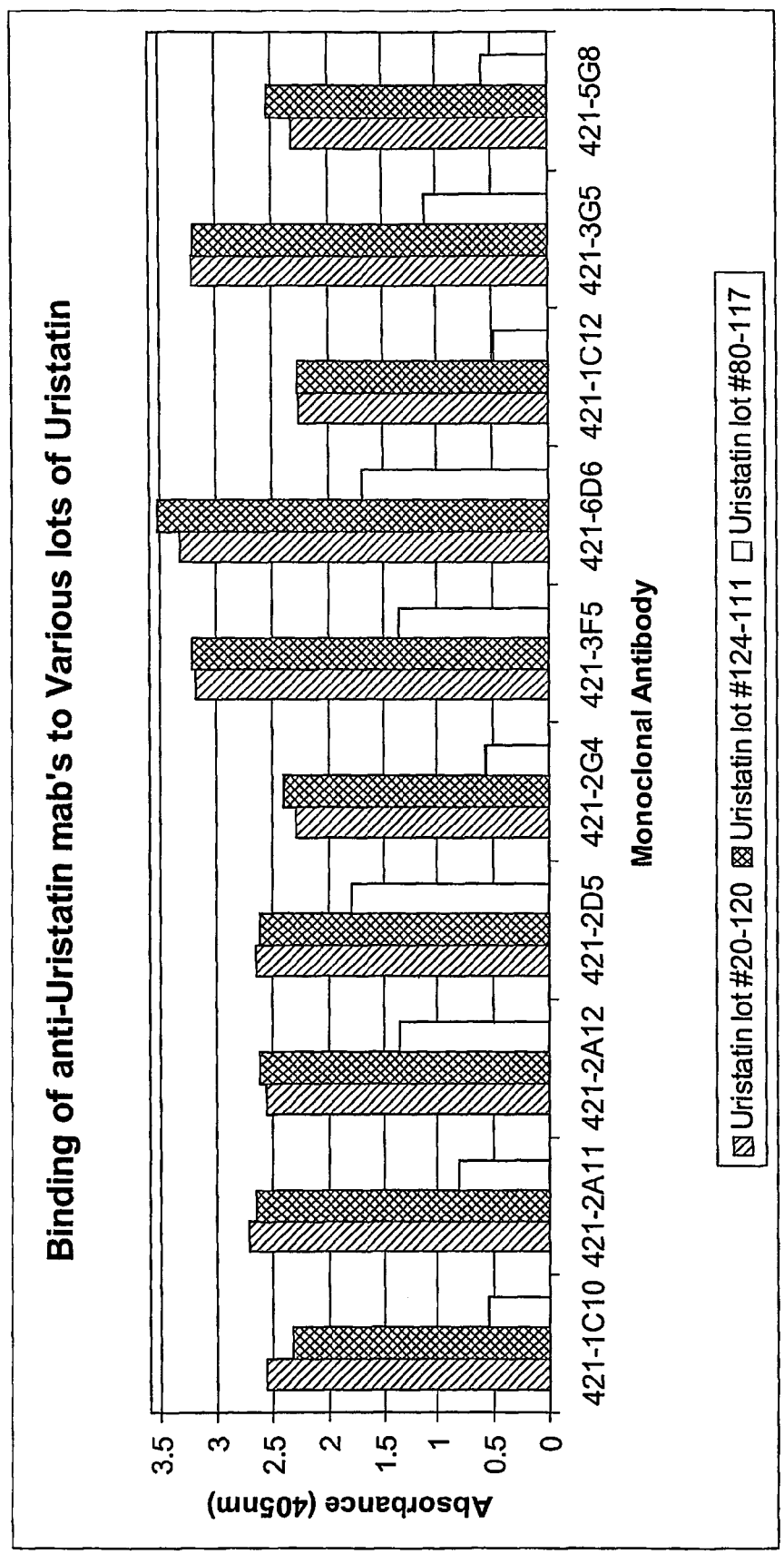
FIG. 2 is a second bar chart of the results of Example 5.

In Example 3, three monoclonal antibodies were tested for their response to three lots of purified UTIs. This example reports the same monoclonal antibodies, along with an additional sixteen monoclonal antibodies. The results are shown in FIGS. 1&2, a series of bar graphs.

The same three lots of purified UTIs were used. UTI lot 20-120 contained 10% of 2-12 kDa proteins (Uristatin 1 & 2), 15% of 17 kDa proteins (Uristatins), 45% of 35 kDa proteins (bikunin), and 30% of 60-80 kDa (AMBK or THP) proteins. UTI lot 124-111 had about 80% of the material as the 17.4 kDa band (Uristatin) but also contained amounts (10%) of Uristatin-1 and 2 (5.9 kDa) and 10% of Bikunin (30.9 kDa) but no AMBK was seen to be present. UTI lot 80-117 containing substantially only the 17 kDa Uristatin material and <2% of other molecular weight ranges.

It can be seen that the lot containing substantially only 17 kDa material was generally bound less strongly than those lots that contained low and high molecular weight species. However, additional monoclonal antibodies were found to bind all three lots in a manner similar to that of the polyclonal antibody control (for example 421-1D11, 421-5B9, and 421-2D5 and would be expected to be similar to 421-3G5. Several antibodies were found to bind the three lots similarly to 421-5G8, for example 421-1C10, 421-1C12, 421-2A11, and 421-2G4. The notable exception was again confirmed with monoclonal antibody 420-5 D11, which showed an affinity for lot 20-120, but not for lots 124-111 and 80-117. It can be concluded that monoclonal antibody 420-5 D11 did not bind strongly to the lower molecular weight uristatin (17 kDa) and bikunin (35 kDa) but preferred the higher molecular weight material (60-80 kDa THP and AMBK are in this range). 420-5D11 was the only monoclonal antibody from the fusion designated 420 (the others were derived from fusion 421). Its distinctive behavior suggested further testing of monoclonal antibodies, which is reported in Example 6.

EXAMPLE 6

Figure 3:
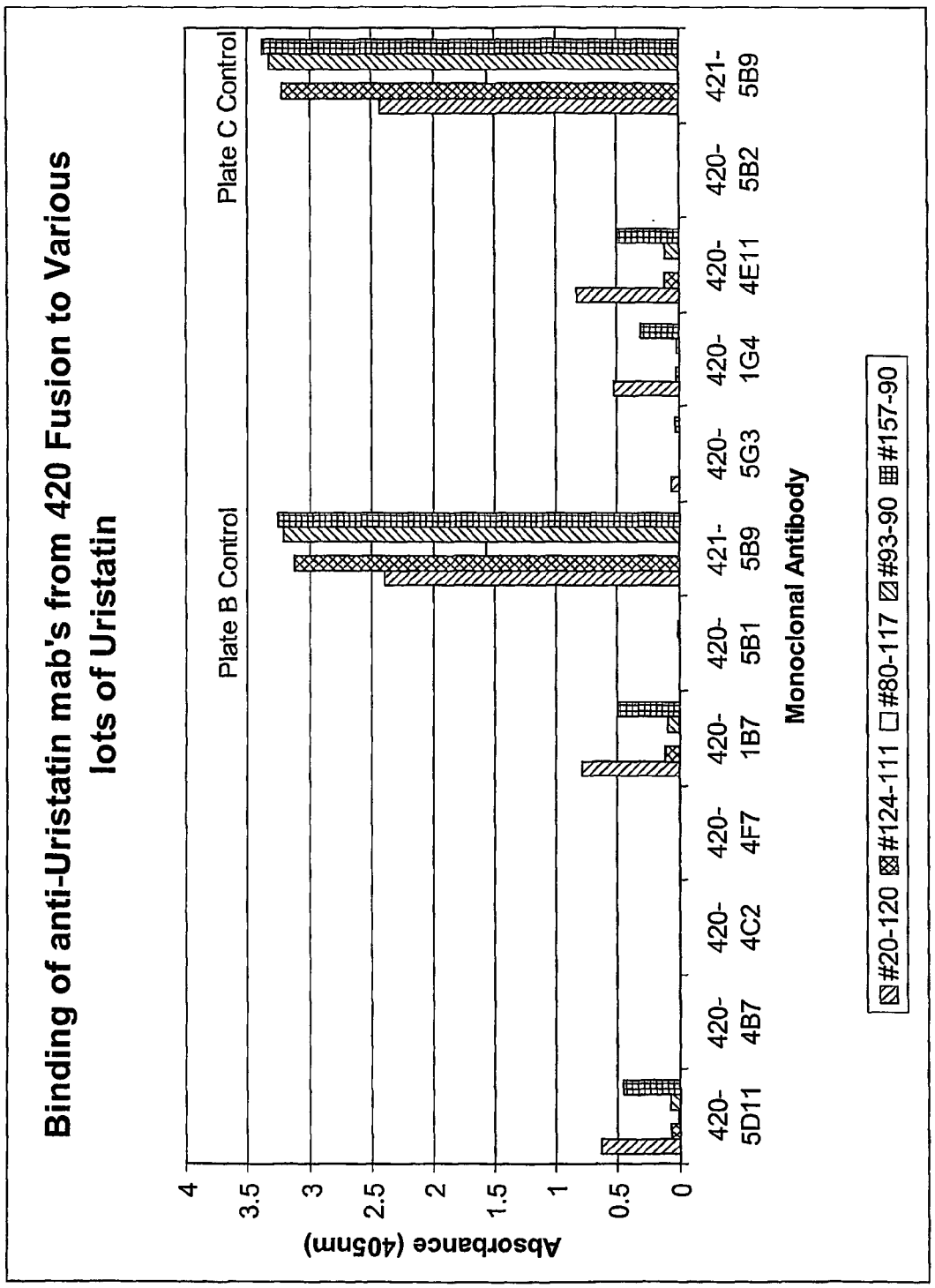
FIG. 3 is a bar chart of the results of Example 6.

Nine monoclonal antibodies from fusion 420 were tested in addition to 420-5D11. Five lots of UTI's were used. Lots 20-120, 124-111, and 80-117 were included again and lots 93-90 and 157-90 were added. The results shown in FIG. 3 show that monoclonal antibody 420-5D11 was similar to 420-1B7, 420-104, and 420-4E11, The other monoclonal antibodies showed substantially no binding of the UTIs. The control used in these experiments was a monoclonal antibody from fusion 421 (421-5B9) that had been found to have a binding profile similar to the polyclonal antibodies but without pro-inhibitor binding, that is, the monoclonal antibody of 421-5B9 binds to each of the UTI lots strongly.

EXAMPLE 7

Two samples of purified total UTIs used in the previous ELISA tests and two samples from patients were reacted with the three representative monoclonal antibodies and one polyclonal antibody and analyzed to determine the proteins binding to the antibodies, using Surface Enhanced Laser Desorption/Ionization (SELDI®) technology (PBS II SELDI® mass spectrometer from Ciphergen, Fremont, Calif. Binding was measured on two types of surfaces using a standard incubation procedure (High Binding PS20 Chip and a low binding RS100 Chip). The signal to noise (S/N) was determined for each mass bound to the antibody as a measure of significance.

Also analyzed by mass spectroscopy were two urine samples from patient 4 and 20 patient 5 reacted with antibodies. Both patients were affected by inflammation with elevated white blood cells (by complete blood cell count), C-reactive protein (by high sensitivity immunoassay), ESR (erythrocyte sedimentation rate), urinalysis (by ten panel MULTISTIX PRO® dip strip) and total urinary trypsin inhibitors (by inhibitor assays). Patient 5 was positive for a blood bacterial infection (toximia) and patient 4 was positive for a urinary bacterial infection (Urinary tract infection) both by microbiological cultures.

The procedure followed is outlined as follows:

1. Three μL of 50 mM $NaHCO_3$ (pH 8.0) was added to each spot on the protein chip, which was covered by a plate to form sample wells.

2. One μL of 1 mg/mL of the antibody was added to each spot and incubated at room temperature for 2 hours with shaking in a humidity chamber.

3. The solution was removed from each spot and the spot was washed twice with 5 μL of washing buffer, phosphate buffered saline (PBS+0.5% Triton detergent).

4. The unbound sites were blocked with 5 μL or 2 mg/mL BSA (bovine serum albunim) or 1 M ethanolamine.

5. After incubation at room temperature, the BSA or ethanolamine were discarded.

6. The spots were twice washed with 5 μL of washing buffer (PBS+0.5% Triton).

7. Five μL of PBS was added to each spot and the chips were placed in a bioprocessor. An additional 10 μL of PBS was added in each well.

8. Ten μL of the sample to be tested (or PBS as a control) was added to each well, then the wells were sealed and shaken at 4° C. overnight.

9. The wells were washed twice with washing buffer and PBS and then shaken at room temperature for 2 minutes.

10. The wells were rinsed twice with 300 μL of deionized water saturated with sinapinic acid.

11. The chips containing the antibodies and samples were analyzed by surface enhanced laser desorption/ionization (SELDI®).

The SELDI® results for the four antibodies are reported in the Table 3 and 4. The results are the masses of proteins bound to the antibodies after exposure to the UTIs in the patients and purified samples. The high sensitivity of this method demonstrates antibody binding to a great many more forms than were detected by the ELISA method. The abundance of forms is expected from the fragmentation, elongation and aggregation that is responsible for the molecular weight ranges for the functional classes of UTI. This method identified exactly the forms bound and does not rely on any interpretation by the composition of the standard Therefore even though protein bound might be a small percentage of the composition, it will be detected if there is binding to the antibody. Antibody binding epitopes are typically small, on the order of 2 to 5 kDa, when antibodies bind to the peptide or glycoprotein sequence in favor of the tertiary structure of the protein sequences. Therefore a common sequence would be expected to be repeated in all variations and the ability of SELDI® to detect all binding events allows a great many variations to be demonstrated. Results from all samples are combined and organized by functional protein groups according to the observed molecular weight falling within ranges for Uristatin 1 or 2, Uristatin, Bikunin, AMBK, THP and the pro-inhibitors. Those binding events of high affinity, frequency or importance are in bold face as determined by signal-to-noise ratios of binding events. The primary binding events are in bold face and underlined. Weak binding events are in plain text to document variations in the proteins. These represent very weak cross-reactivities of the type that would not impact an immuno-assay if properly formated.

TABLE 3

SELDI ® Results Comparison of Three Novel Monoclonal Antibodies for UTIs versus a Standard Polyclonal Antibody for a total measurement of all UTI and pro-inhibitors using purified UTI standards.

| | UTI Functional Group | | | |
|---|---|---|---|---|
| | 1Mab 421-3G5 IUTI clone | Mab 421-5G8 Uristatin clone | Mab 420-5D11 THP clone | polyclonal Rb Anti-Uristatin IUTI and Pro-UTI |
| Uristatin 1 or 2 - (average molecular weights of 5.9 & 8.5 kDa with kDa range 2-12) | 3.48, 3.86 | 3.48, 3.86 | 3.48, 3.86 | 3.49, 3.86 |
| Uristatin (17 kDa, range 11-22) | 15.9, 17.8, 16.3, 18.0 | 15.9, 18.3 | 15.9, 16.3 18.2 | 15.9, 17.8 |
| Bikunin (33 kDa, range 21-46) | No significant peaks | No significant peaks | 41.5, 48.1 | 42.5, 42.6 |
| AMBK (66 kDa, range 42-70) | 62.9, 62.5, | No significant peaks | 67.1 | 66.6, 66.7 |
| THP (85 kDa, 80-91 kDa) | 81.9 | 81.7 | 81.7 | 82.6 |
| p-alpha-I (125 kDa) | No significant peaks | 122.6 | No significant peaks | 108.6, 120.0, 142.7 |
| I-alpha-I (220 kDa) | No significant peaks | No significant peaks | No significant peaks | No significant peaks |

TABLE 4

SELDI ® Results Comparison of Three Novel Monoclonal Antibodies for UTIs versus a Standard Polyclonal Antibody for a total measurement of all UTI and pro-inhibitors using purified patient samples.

| | IUTI Functional Group | | | |
|---|---|---|---|---|
| | Mab 421-3G5 IUTI clone | Mab 421-5G8 Uristatin clone | Mab 420-5D11 THP clone | polyclonal Rb Anti-Uristatin IUTI and Pro-UTI |
| Uristatin or 2 - (average molecular weights of 5.9 & 8.5 I kDA with kDa range 2-12) | 2.82, 3.41, 3.48, 5.38, 5.57 6.30, 7.24, 3.5, 3.8, 4.0, 5.6, 6.0, 6.3, 8.0, 9.2, 9.8, 10.9 | 2.82, 3.41, 3.48, 4.0, 5.4, 7.2, 9.18 9.85 | 2.82, 3.0, 3.5, 4.7, 3.7, 5.4, 5.6, 7.2, 3.7, 10.8 | 2.8, 5.0, 5.4, 7.2, 10.7, 3.5, 4.0, 5.9 6.0, 6.3, 8.1, 10.7 |

TABLE 4-continued

SELDI ® Results Comparison of Three Novel Monoclonal Antibodies for UTIs versus a Standard Polyclonal Antibody for a total measurement of all UTI and pro-inhibitors using purified patient samples.

| | IUTI Functional Group | | | |
|---|---|---|---|---|
| | Mab 421-3G5 IUTI clone | Mab 421-5G8 Uristatin clone | Mab 420-5D11 THP clone | polyclonal Rb Anti-Uristatin IUTI and Pro-UTI |
| Uristatin (17 kDa, range 11-22) | 11.8, 18.0, 16.3, 13.4, 14.0 | 12.0, 14.0, 13.5, 21.1 | 11.9, 13.5, 21.1, | 13.4, 14.0, 16.3 |
| Bikunin (33 kDa, range 21-46) | 21.1, 33.6, 35.2, 33.5, 45.9 | 23.0, 22.7 | 23.3, 41.6 | 21.2, 22.6, 23.3, 33.4, 33.1 35.2, 42.3 |
| AMBK (66 kDa, range 42-70) | 67.0 | No significant peaks | No significant peaks | 58.6 |
| THP (85 kDa, 80-91 kDa) | 81.9, 91.1 | No significant peaks | 80.2, 80.6 81.9 | 82.6, 79.2 |
| p-alpha-I (125 kDa) | No significant peaks | 128.5, 132.1 | No significant peaks | 101.1, 103.7, 106.3, 120.0, 1234, 133.0, 142.7 |
| I-alpha-I (220 kDa) | No significant peaks | No significant peaks | No significant peaks | No significant peaks |

Mass differences were rounded to nearest 0.1 kDa. Peaks with highest Signal to Noise ratios (S/N) relative to other peaks are reported. Low S/N observations were eliminated from table. The table represents most but not all possible forms. Spectra also showed peaks at 66.9 to 66.6 and 33.3 and 133.0 to 133.9 that were due to albumin used in the blocking procedure for the SELDI analysis. When triethanolamine was used to block chips those peaks were not observed.

The results demonstrated that the three types of monoclonal antibodies detect different patterns of UTIs and these patterns include a range of variants. The monoclonal antibodies are specific for UTIs whereas the polyclonal antibodies detect both UTIs and Pro-inhibitors. We can not see all the urinary trypsin inhibitor fragments that the clones detect in the patterns represented in the SDS gels. The gel method is not sensitive enough to report all of the UTIs the antibody can bind. More of the fragments actually bound are shown in the SELDI® data. All fragments bound are not listed as additional variations would be found as different patients are tested. The extent or strength of binding to a given UTI was estimated relative to other UTIs. The strongest binding by smallest fragments are the best representation of the epitopes bound by each antibody. The low molecular weight sequences in the Uristatin 1 or 2 functional groups are the smallest linear sequence with strong binding.

In Tables 3 and 4 using purified standards and patients, the primary binding for Mab 421-3G5 was strong for Uristatin-1 or -2, Uristatin, Bikunin, and AMBK and much less strong for THP with no significant pro-inhibitor binding. The primary binding for Mab 421-5G8 was with Uristatin-1 or -2, less for Uristatin and much less strong for THP or Bikunin or pro-inhibitors. The primary binding for Mab 420-5D11 was strong for THP, Uristatin, and Uristatin-1 or -2, less strong for Bikunin or AMBK. The polyclonal binding was with all forms including the pro-inhibitors. These results were as expected based on SDS gels. The SELDI® results however also demonstrated that all three antibodies bound to Uristatin-1 or -2 in the standards very strongly at 3.9, and with high affinity at 2.8 and 3.5. The SELDI® results also show several low affinity binding events, not strong enough to hinder specificity, but measurable.

The results in Table 4 using individual patient samples, demonstrate the same 25 primary binding patterns for Mab 421-3G5, Mab 421-5G8, Mab 420-5D11 and the polyclonal shown with the standards. Again these results were as expected based on SDS gels. The SELDI® results however also demonstrated that all three antibodies strongly bound to several new forms of Uristatin-1 or -2, Uristatin, Bikunin and AMBK within the expected ranges for each. In particular primary binding to 2.8, 5.4, 7.2, 11.8, 21.1, and 67.0 kDa were observed in patient samples but not in the purified standards. This demonstrated the variations expected in pathological conditions for reasons previous stated. The lack of these peaks in the purified standards is the result of the pooling of many patient and purification of specimens to the target molecular weight targets of 15, 30 and 60 kDa. The SELDI® also showed at least some cross-reactivity to THP in the polyclonal and Mab 420-5D11 case.

EXAMPLE 8

Four proteins, Human Serum Albumin (HSA), Tamm-Horsfall protein (THP), α-1-microglobulin (α-i M), and α-i-antichymotrypsin (α-i ACT) were tested for crossreactivity in the Uristatin sandwich ELISA test. These proteins were chosen either because of their high concentration in urine or because they were suggested as possible cross reactants during the western blot or SELDI® work that used these antibodies with urine samples. Cross reactivity studies were done in a competitive format to allow relative binding to be compared. For example the binding of antibodies to uristatin was significantly stronger than to THP, the assay for uristatin was not interfered with by THP. The only proteins and antibodies found to be cross-reactive in the competitive sandwich ELISA test was THP with Mab 420-5D11 and the polyclonal antibody (See Table 5).

TABLE 5

Cross-reactivity Results Comparison of Three Novel Monoclonal Antibodies for UTIs versus a Standard Polyclonal Antibody using purified protein standards.

| Antibody | Crossreactivity Result for Proteins Tested | | | |
|---|---|---|---|---|
| | HSA | THP | α-1MG | α-1ACT |
| Mab 421-3G5 | none | none | none | none |
| Mab 421-5G8 | none | none | none | none |
| Mab 420-5D11 | none | = approx. 100% | none | none |
| Rb-anti-Uristatin | none | >=50% | none | none |

The broad objective of the invention is to provide a method for conveniently testing the urine of medical patients to identify the presence of diseases by their association with inhibitory urinary trypsin inhibitors (UTI). It has been previously noted that the presence in urine of UTIs indicates disease. Heretofore, it has not been possible to relate particular UTIs with certain diseases since the UTIs generally were measured in the aggregate, rather than individually. The present inventors have developed monoclonal antibodies using samples of UTIs isolated from the urine of known renal disease patients and associated the monoclonal antibodies with the various fragments of the non-inhibitor precursors of UTIs. As the examples have shown, the monoclonal antibodies have been found to have varying responses to the samples of UTIs, which enable one to identify their preference for certain of the UTIs. Additional investigation by mass spectroscopy has extended the information available about the composition of the UTI samples and the response of the monoclonal antibodies to them. One important finding has been the discovery that a lower molecular weight UTI fragments, at about 2.8, 3.5, 3.9 and 5.4 kDa was an important component in the total UTIs observed in samples. That result was not seen in SDS-Page testing as only the proteins with the highest concentration are visualized and consequently the results of ELISA testing with the monoclonal antibodies could not be completely interpreted. Since the use of mass spectroscopy in routine clinical work is impractical, the present inventors have applied the information obtained from mass spectroscopy to interpretation of the results of ELISA tests, which may be more readily used in clinical settings.

The proposed procedures for testing urine samples may be outlined as follows:
1. Prepare monoclonal antibodies against known sources of one or more UTIs.
2. Test the monoclonal antibodies against the known sources of UTIs and select those that are found to have a preference for UTIs having known molecular weights.
3. Add the selected monoclonal antibodies to a sample of urine containing unknown amounts of UTIs and determine which UTIs are present and their relative amounts.
4. Correlate the UTIs determined in step 3 with a disease associated with the measured distribution of UTIs.

The UTIs that have been identified by SDS-PAGE methods and correlated with ELISA tests include fragments of the I-α-I and P-α-I non-inhibitors that have typical average molecular weights of about 66 kDa (AMBK), 30 kDa (Bikunin or HI-30), 17 kDa (Uristatin), 5 kDa (Uristatin-1), 8 kDa (Uristatin-2) and ranges defined around these averages due to fragmentation, variation and aggregation. In particular, it was found also that smaller fragments having molecular weights of about 2 to 5 kDa were present. Those were designated as fragments of Uristatin-1 and 2. It now appears from mass spectroscopy that fragments at about 2.8, 3.5, 3.8 and 5.0 kDa are present in samples and bound by antibodies, but not clearly shown by the SDS-PAGE results.

The monoclonal antibodies appeared to be grouped in their response to samples containing known distributions of particular UTIs. That is, some appeared to bind to UTI samples containing significant amounts of 2-12 kDa fragments (Uristatin 1 or 2), while others appeared to bind to UTI samples containing a large fraction of AMBK, Bikunin or the Uristatin fractions of 62, 30 and 17 kDa. Still others bound to Bikunin, Uristatin fractions and THP common sequence. Three monoclonal antibodies were selected as characteristic of their groups and those antibodies were deposited in the ATCC depository. Other monoclonal antibodies having similar properties are identified and their performance reported in the examples for further information.

The advantage of identifying monoclonal antibodies having a preference for certain UTIs is of course that it opens the possibility of distinguishing certain diseases or other medical problems with a particular distribution of UTI fragments. Certain antibodies may be specific for binding certain UTI fragments or for certain combinations of fragments. Then, by using those monoclonal antibodies in ELISA or other such tests it will be possible to identify which of the UTIs are present and their relative proportions.

What is claimed is:

1. A method of assaying a biological fluid for urinary tryspin inhibitors (UTI) selected from the group consisting of uristatin, uristatin-1, uristatin-2 and THP comprising contacting a sample of biological fluid with a monoclonal antibody against purified uristatin and detecting said UTIs bound by said monoclonal antibody.

2. A method of claim 1, wherein said monoclonal antibody is secreted by a hybridoma selected from the group consisting of ATCC 421-5G8.1A8.5C1, ATCC 420-5D11.5G8.1E4, and ATCC 421-3G5.4C5.3B6.

3. A method of claim 2, wherein said monoclonal antibody is secreted from hybridoma ATCC 421-5G8.1A8.5C1.

4. A method of claim 2, wherein said monoclonal antibody is secreted from hybridoma ATCC 420-5D11.1E4.

5. A method of claim 2 wherein said monoclonal antibody is secreted from hybridoma ATCC 421-3G5.4C5.3B6.

6. A method of claim 2 wherein said UTIs are detected in an immunoassay.

7. A method of claim 6 wherein said immuno assay is selected from the group consisting of MIC (microparticle capture immunoassays, LAI (latex agglutination inhibition), IC (solid phase chromatographic), RIA (radio immunoassays), ELISA (enzyme linked immunoabsorbent assay), BIA (enzyme linked assays), FIA (fluorescence linked assays), LIA (luminescence linked assays), CLA (chemiluminescence assays), OA (optical color label assays), EST (electrochemical signal transducers) and rare earth metals label assays.

8. A method of claim 1 wherein said biological fluid is urine.

9. A method of claim 1 wherein said biological fluid is blood plasma.

* * * * *